(12) United States Patent
Lei

(10) Patent No.: US 9,925,539 B2
(45) Date of Patent: Mar. 27, 2018

(54) FLUID RAPID TESTING DEVICE

(71) Applicant: Zhejiang OrientGene BioTech Co. Ltd., La Jolla, CA (US)

(72) Inventor: Siyu Lei, Anji (CN)

( * ) Notice: Subject to any disclaimer, the term of this patent is extended or adjusted under 35 U.S.C. 154(b) by 175 days.

(21) Appl. No.: 15/139,650

(22) Filed: Apr. 27, 2016

(65) Prior Publication Data

US 2017/0151557 A1    Jun. 1, 2017

(30) Foreign Application Priority Data

Nov. 26, 2015   (CN) .......................... 2015 1 0843136

(51) Int. Cl.
*B01L 3/00* (2006.01)
*A61B 10/00* (2006.01)
*A61F 13/38* (2006.01)

(52) U.S. Cl.
CPC .......... *B01L 3/508* (2013.01); *A61B 10/0096* (2013.01); *A61F 13/38* (2013.01); *B01L 2200/08* (2013.01); *B01L 2200/085* (2013.01); *B01L 2300/043* (2013.01); *B01L 2300/069* (2013.01)

(58) Field of Classification Search
CPC ............... B01L 3/508; B01L 2300/069; B01L 2300/043; B01L 2200/085; B01L 2200/08; A61F 13/38; A61B 10/0096
See application file for complete search history.

(56) References Cited

U.S. PATENT DOCUMENTS

2011/0171754 A1*  7/2011  Redmond ......... B01L 3/502715
                                                        436/518
2012/0076565 A1*  3/2012  Cocchioni ............ A45D 29/007
                                                        401/125

\* cited by examiner

*Primary Examiner* — Dennis White
(74) *Attorney, Agent, or Firm* — Buche & Associates, P.C.; John K. Buche; Bryce A. Johnson

(57) ABSTRACT

Disclosed is fluid rapid testing device, comprising: a box body having transparent side walls, a box cover cooperating with an opening of the box body, and a protection cover hinged to the box cover; wherein the testing device further comprises: a fluid sampling swab, a fluid collection chamber operable to accommodate the fluid sampling swab and collect a fluid on the fluid sampling swab, and a fluid collection groove in communication with a bottom of the fluid collection chamber; and a testing strip extending into the fluid collection groove is arranged on at least one inner wall of the box. The testing device according to the present invention has a simple structure and operation convenience. The box body of the testing device may be conveniently and quickly opened or closed, a small amount of fluid is needed, the sampling process is simplified, and the fluid may also be conveniently taken out for subsequently-desired tests.

10 Claims, 3 Drawing Sheets

FLUID RAPID TESTING DEVICE

CROSS-REFERENCE TO RELATED APPLICATIONS

This application claims priority to Chinese Patent Application No. 201510843136.3 filed on Nov. 26, 2015, the content of which is incorporated herein by reference.

FIELD OF THE INVENTION

The present invention relates to the field of testing devices, and in particular, relates to a fluid rapid testing device.

BACKGROUND OF THE INVENTION

In the fields of medical diagnosis and legal identification, a body fluid test is very commonly used. A sample of a liquid to be tested is collected by using a testing device or a testing cup, and it is judged whether the liquid sample contains an analyte, which is a customary method in the field. Such testing device or testing cup generally requires that the sample collected in a sample container. A testing technician inserts a testing reagent strip into the sample and make sure that the reagent strip is partially immersed in the sample, and takes out the reagent strip and reads a test result a period of time later. In such testing, the testing technician may contact the sample, which may cause hazards to the health or cause the sample to be contaminated. In addition, under special conditions, operations are hard to be completed.

Chinese Patent Application CN204514923U has disclosed a body fluid testing cup. The testing cup comprises: a cup body, a test paper card, and a cover film; wherein the test paper card is arranged inside the cup body and is provided with a test paper insertion groove for accommodating a test paper strip, and the cover film covers an opening face of the test paper insertion groove. The cup body is internally provided a limiting member for fixing the test paper card, wherein at least two limiting members are used. According to this patent application, the test paper card is more securely fixed, thereby preventing the test paper card from moving about in the cup body; and during reading of a test result from the outside of the cup body, visual error may not simply occur, and the reading of the test result is not affected. However, this testing cup needs a large volume of body liquid, and thus it is difficult to sample such less-produced body liquids as saliva. In addition, in case of a viscous liquid, the liquid has poor fluidity and thus the testing efficiency is low.

SUMMARY OF THE INVENTION

An objective of the present invention is to provide a fluid rapid testing device, which is simple in structure and convenient in operation, and may be conveniently and quickly opened or closed. In addition, with the testing device, a small amount of fluid is needed, the sampling process is simplified, and the fluid may also be conveniently taken out for subsequently-desired tests. To this end, the present invention employs the following technical solution: a fluid rapid testing device, comprising: a box having transparent side walls, a box cover cooperating with an opening of the box, and a protection cover hinged to the box cover; wherein the testing device further comprises: a fluid sampling swab, a fluid collection chamber operable to accommodate the fluid sampling swab and collect a fluid on the fluid sampling swab, and a fluid collection tank in communication with a bottom of the fluid collection chamber; and a testing strip extending into the fluid collection tank is arranged on at least one inner wall of the box.

According to the above technical solution, a fluid to be tested is sampled by using the fluid sampling swab, and the sampled fluid is input into the fluid collection chamber and is isolated from the outside and sealed, and meanwhile the fluid enters the fluid collection tank and is in contact with the testing strip, thereby completing the test.

Preferably, the fluid sampling swab comprises an operation portion arranged outside the fluid collection chamber, a connection portion with a sampling body arranged on a tail end thereof, and a transitional neck portion connecting the connection portion to the operation portion; wherein the operation portion has a diameter greater than an inner diameter of the fluid collection chamber, and the transitional neck portion is adaptively connected to a mouth portion of the fluid collection chamber.

By practicing the technical solution, when the fluid sampling swab is inserted into the fluid collection chamber, the fluid sampling swab is directly adapted to the mouth portion of the fluid collection chamber via the transitional neck portion. After the fluid sampling swab is inserted into the fluid collection chamber, a specific external force is needed to be applied to pull out the fluid sampling swab from the fluid collection chamber. In addition to facilitating the operations, the operation portion has a diameter greater than the inner diameter of the fluid collection chamber, which further isolates the outside from the interior of the fluid collection chamber, and ensures that the fluid is free of contamination.

Preferably, an installation portion is arranged on a tail end of the connection portion, and the sampling body is installed on the installation portion.

Preferably, a sealing ring in close contact with an inner wall of the fluid collection chamber is arranged on an outer ring of the installation portion.

Preferably, the fluid sampling swab is provided with a gas exhaust passage axially passing through a body of the fluid sampling swab, wherein when the fluid sampling swab is pushed downwards by applying a force to extrude the fluid on the sampling body, the air inside the chamber may be exhausted via the gas exhaust passage, thereby ensuring that the fluid smoothly enters the fluid collection tank.

Preferably, the fluid collection chamber has a chamber mouth 1 to 5 mm higher than an upper surface of the box cover, which facilitates removing of the fluid sampling swab and isolation of the fluid collection chamber from the outside, and saves materials.

Preferably, the fluid collection chamber and the box cover form an integral structure, which enhances the strength and simplifies the process.

Preferably, an installation groove positioned at an end portion of the fluid collection tank is arranged on an inner wall of the box, an installation sheet being installed in the installation groove; and the testing strip is installed on the installation sheet.

Preferably, the connection portion is in a hollow structure, which saves the materials and reduces the manufacture cost.

Preferably, the operation portion comprises an outer operation ring, an intermediate post arranged inside the outer operation ring and communicated with both outside and the fluid collection chamber, and a reinforcement rib arranged between the intermediate post and an inner wall of the outer operation ring.

By practicing the above technical solution, the testing device according to the present invention has a simple structure and operation convenience. The box of the testing device may be conveniently and quickly opened or closed, a small amount of fluid is needed, the sampling process is simplified, and the fluid may also be conveniently taken out for subsequently-desired tests.

Figure 1:
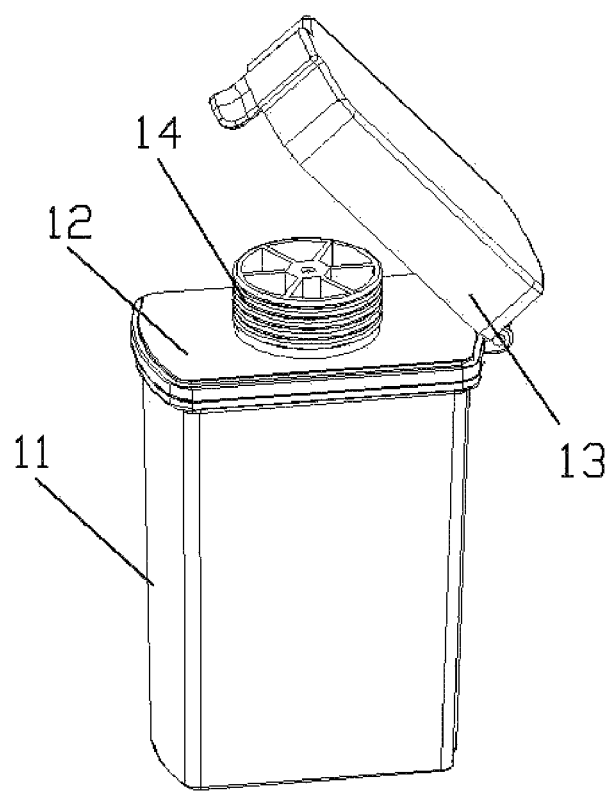
FIG. 1 is a schematic structural view of a fluid rapid testing device according to an embodiment of the present invention.

In the drawings, 11 denotes a box, 111 denotes an installation groove, 12 denotes a box cover, 13 denotes a protection cover, 14 denotes a fluid sampling swab, 141 denotes an operation portion, 142 denotes a connection portion, 143 denotes a transitional neck portion, 144 denotes an installation portion, 1441 denotes a sealing ring, 15 denotes a fluid collection chamber, 16 denotes a fluid collection tank, 2 denotes a testing strip, and 3 denotes a sampling body.

DETAILED DESCRIPTION OF THE INVENTION

The present invention is described hereinafter in detail with reference to the attached drawings and specific embodiments.

Embodiment 1

Figure 2:
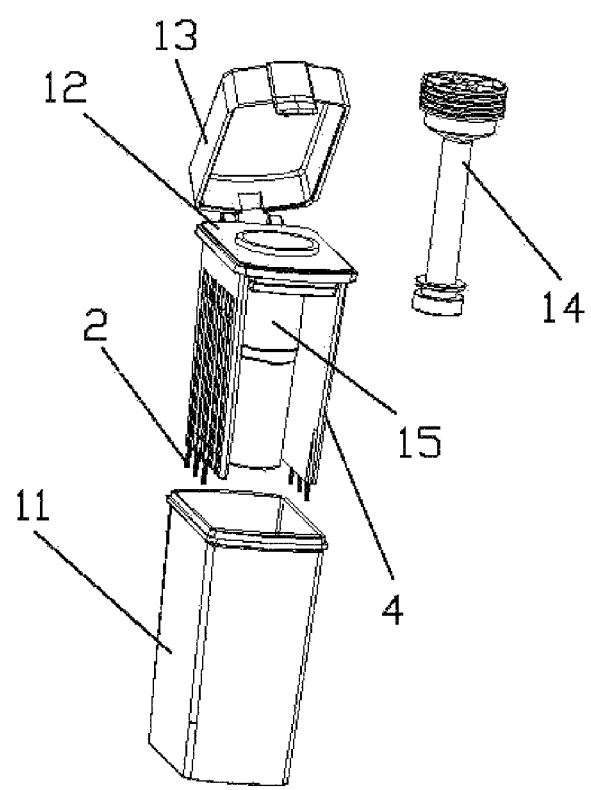
FIG. 2 is a schematic exploded view of a fluid rapid testing device according to an embodiment of the present invention.
Figure 4:
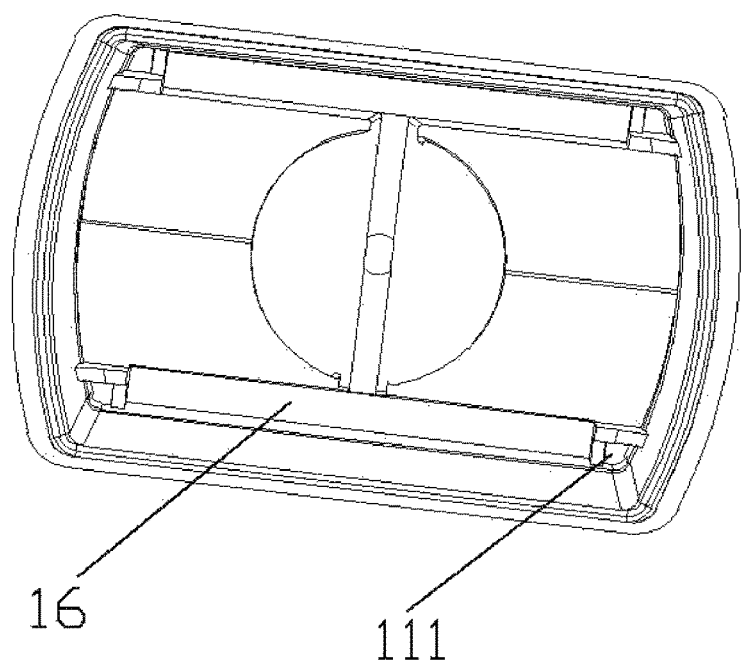
FIG. 4 is a schematic exploded view of a box according to an embodiment of the present invention.

This embodiment provides a fluid rapid testing device. As illustrated in FIG. 1, the testing device comprises: a box body 11, a box cover 12 cooperating with an opening of the box body 11, and a protection cover 13 hinged to the box cover 12. The box cover is mainly to isolate the interior of the box body 11 from the outside, and the protection cover 13 is to achieve protection and further enhance the isolation, thereby ensuring that a fluid sample is free of contamination and that a testing structure is accurate. As illustrated in FIG. 2, the testing device further comprises: a fluid sampling swab, a fluid collection chamber 15 operable to accommodate the fluid sampling swab 14 and collect a fluid on the fluid sampling swab 14, and a fluid collection tank 16 in communication with a bottom of the fluid collection chamber 15; wherein an installation sheet 4 is arranged on each of two opposing inner walls of the box body 11, a testing strip 2 extending into the fluid collection tank 16 being arranged inside the installation sheet 4. The fluid collection tank 16 is arranged at a bottom of the box body 11. As illustrated in FIG. 4, a cylindrical collection portion is arranged at the bottom of the box body 11, wherein the collection portion has a pore diameter slightly greater than a pore diameter of a lower opening of the fluid collection chamber 15, the collection portion is in communication with the fluid collection tank 16, and an interior of the collection portion forms an arc shape towards a chamber portion of the collection portion, which facilitates downward flowing of the fluid. A fluid to be tested is sampled by using the fluid sampling swab 14, and the sampled fluid is input into the fluid collection chamber 15 and is isolated from the outside and sealed, and meanwhile the fluid enters the fluid collection tank 16 and is in contact with the testing strip 2, thereby completing the test.

Figure 3:
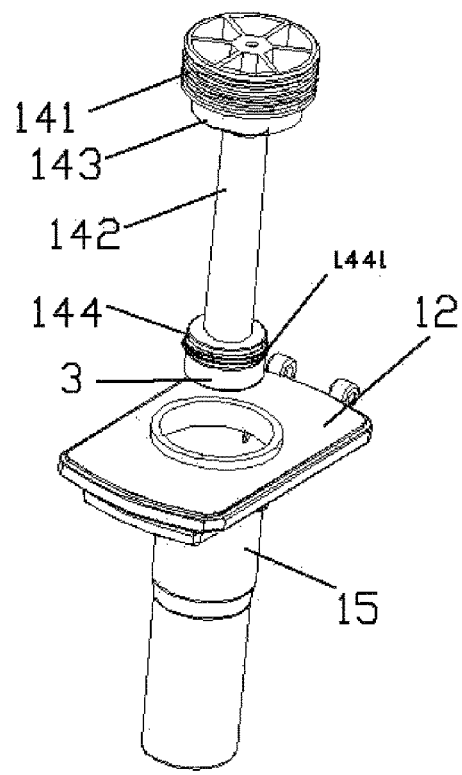
FIG. 3 is a schematic exploded view of a fluid sampling swab according to an embodiment of the present invention.

For ease of operations, the fluid collection chamber 15 may be rapidly opened or closed, and the structure of the fluid sampling swab 14 is improved. As illustrated in FIG. 3, the fluid sampling swab 14 comprises: an operation portion 141 arranged outside the fluid collection chamber 15, a connection portion 142 with an installation portion 144 arranged on a tail end thereof, and a transitional neck portion 143 connecting the connection portion 142 to the operation portion 141. A sampling body 3 is fixed on the installation portion 144, wherein the sampling body 3 may be a structure which is capable of absorbing a liquid and extruding the liquid when a force is applied, for example, cotton, sponge or the like. The operation portion 141 has a diameter greater than an inner diameter of the fluid collection chamber 15. The transitional neck portion 143 is adaptively connected to a mouth portion of the fluid collection chamber 15. When the fluid sampling swab 14 is inserted into the fluid collection chamber 15, the fluid sampling swab 14 is directly adapted to the mouth portion of the fluid collection chamber 15 via the transitional neck portion 143. After the fluid sampling swab 14 is inserted into the fluid collection chamber 15, a specific external force is needed to be applied to pull out the fluid sampling swab 14 from the fluid collection chamber 15. In addition to facilitating the operations, the operation portion has a diameter greater than the inner diameter of the fluid collection chamber 15, which further isolates the outside from the interior of the fluid collection chamber 15, and ensures that the fluid is free of contamination. To further ensure the sealing performance, a sealing ring 1441 in close contact with an inner wall of the fluid collection chamber 15 is arranged on an outer ring of the installation portion 144. When the fluid sampling swab 14 is downward extruded, due to presence of a specific amount of air in the fluid collection chamber 15, a greater extrusion force is needed. As a result, the fluid may not be simply extruded to flow into the fluid collection tank 16. In this case, the fluid sampling swab 14 is provided with a gas exhaust passage axially passing through a body of the fluid sampling swab 14, which solves this problem.

Embodiment 2

This embodiment provides a fluid rapid testing device. The testing device comprises: a box body 11, a box cover 12 cooperating with an opening of the box body 11, and a protection cover 13 hinged to the box cover 12. The box cover 13 is mainly to isolate the interior of the box body 11 from the outside, and the protection cover 13 is to achieve protection and further enhance the isolation, thereby ensuring that a fluid sample is free of contamination and that a testing structure is accurate. The testing device further comprises: a fluid sampling swab, a fluid collection chamber 15 operable to accommodate the fluid sampling swab 14 and collect a fluid on the fluid sampling swab 14, and a fluid collection tank 16 in communication with a bottom of the fluid collection chamber 15; wherein an installation sheet 4 is arranged on each of two opposing inner walls of the box body 11, a testing strip 2 extending into the fluid collection tank 16 being arranged inside the installation sheet 4. The fluid collection tank 16 is arranged on a lateral side of the box body 11. A fluid to be tested is sampled by using the fluid sampling swab 14, and the sampled fluid is input into the fluid collection chamber 15 and is isolated from the outside and sealed, and meanwhile the fluid enters the fluid collection tank 16 and is in contact with the testing strip 2, thereby completing the test.

For ease of operations, the fluid collection chamber 15 may be rapidly opened or closed, and the structure of the fluid sampling swab 14 is improved. The fluid sampling swab 14 comprises: an operation portion 141 arranged outside the fluid collection chamber 15, a connection portion 142 with an installation portion 144 arranged on a tail end thereof, and a transitional neck portion 143 connecting the connection portion 142 to the operation portion 141. A sampling body 3 is fixed on the installation portion 144, wherein the sampling body 3 may be a structure which is capable of absorbing a liquid and extruding the liquid when a force is applied, for example, cotton, sponge or the like. The operation portion 141 has a diameter greater than an inner diameter of the fluid collection chamber 15. The transitional neck portion 143 is adaptively connected to a mouth portion of the fluid collection chamber 15. The fluid collection chamber 15 and the box cover 12 form an integral structure, and the fluid collection chamber 15 has a chamber mouth 1 to 5 mm higher than an upper surface of the box cover 12, which is preferably 2 mm in this embodiment. When the fluid sampling swab 14 is inserted into the fluid collection chamber 15, the fluid sampling swab 14 is directly adapted to the mouth portion of the fluid collection chamber 15 via the transitional neck portion 143. After the fluid sampling swab 14 is inserted into the fluid collection chamber 15, a specific external force is needed to be applied to pull out the fluid sampling swab 14 from the fluid collection chamber 15. In addition to facilitating the operations, the operation portion has a diameter greater than the inner diameter of the fluid collection chamber 15, which further isolates the outside from the interior of the fluid collection chamber 15, and ensures that the fluid is free of contamination. To further ensure the sealing performance, a sealing ring 1441 in close contact with an inner wall of the fluid collection chamber 15 is arranged on an outer ring of the installation portion 144. When the fluid sampling swab 14 is downward extruded, due to presence of a specific amount of air in the fluid collection chamber 15, a greater extrusion force is needed. As a result, the fluid may not be simply extruded to flow into the fluid collection tank 16. In this case, the connection portion 142 is in a hollow structure, and the fluid sampling swab 14 is provided with a gas exhaust passage axially passing through a body of the fluid sampling swab 14, which solves this problem. The operation portion 141 comprises an outer operation ring, an intermediate post arranged inside the outer operation ring and communicated with both outside and the fluid collection chamber 15, and a reinforcement rib arranged between the intermediate post and an inner wall of the outer operation ring.

What is claimed is:

1. A fluid rapid testing device, comprising: a box body, a box cover cooperating with an opening of the box body, and a protection cover hinged to the box cover; wherein the testing device further comprises: a fluid sampling swab, a fluid collection chamber operable to accommodate the fluid sampling swab and collect a fluid on the fluid sampling swab, and a fluid collection tank in communication with a bottom of the fluid collection chamber; and a testing strip extending into the fluid collection tank is arranged on at least one inner wall of the box body.

2. The fluid rapid testing device according to claim 1, wherein the fluid sampling swab comprises: an operation portion arranged outside the fluid collection chamber, a connection portion with a sampling body arranged on a tail end thereof, and a transitional neck portion connecting the connection portion to the operation portion; wherein the operation portion has a diameter greater than an inner diameter of the fluid collection chamber, and the transitional neck portion is adaptively connected to a mouth portion of the fluid collection chamber.

3. The fluid rapid testing device according to claim 2, wherein an installation portion is arranged on a tail end of the connection portion, and the sampling body is installed on the installation portion.

4. The fluid rapid testing device according to claim 3, wherein a sealing ring in close contact with an inner wall of the fluid collection chamber is arranged on an outer ring of the installation portion.

5. The fluid rapid testing device according to claim 1, wherein the fluid sampling swab is provided with a gas exhaust passage axially passing through a body of the fluid sampling swab.

6. The fluid rapid testing device according to claim 1, wherein the fluid collection chamber has a chamber mouth 1 to 5 mm higher than an upper surface of the box cover.

7. The fluid rapid testing device according to claim 6, wherein the fluid collection chamber and the box cover form an integral structure.

8. The fluid rapid testing device according to claim 1, wherein an installation groove positioned at an end portion of the fluid collection tank is arranged on an inner wall of the box body, an installation sheet being installed in the installation groove; and the testing strip is installed on the installation sheet.

9. The fluid rapid testing device according to claim 2, wherein the connection portion is in a hollow structure.

10. The fluid rapid testing device according to claim 2, wherein the operation portion comprises an outer operation ring, an intermediate post arranged inside the outer operation ring and communicated with both outside and the fluid collection chamber, and a reinforcement rib arranged between the intermediate post and an inner wall of the outer operation ring.

* * * * *